US011716964B2

United States Patent
Wu et al.

(10) Patent No.: US 11,716,964 B2
(45) Date of Patent: Aug. 8, 2023

(54) INTELLIGENT DEFECATION DEVICE FOR LIVING CREATURE

(71) Applicant: LuluPet Co., Ltd., Taipei (TW)

(72) Inventors: James Cheng-Han Wu, Taipei (TW); Pei-Hsuan Shih, Taipei (TW); Chun-Ming Su, Taipei (TW); You-Gang Kuo, Taipei (TW); Ning-Yuan Lyu, Taipei (TW); Chi-Yeh Hsu, Taipei (TW); Liang-Hao Huang, Taipei (TW)

(73) Assignee: LULUPET CO., LTD., Taipei (TW)

( * ) Notice: Subject to any disclaimer, the term of this patent is extended or adjusted under 35 U.S.C. 154(b) by 219 days.

(21) Appl. No.: 16/899,557

(22) Filed: Jun. 11, 2020

(65) Prior Publication Data

US 2021/0007320 A1    Jan. 14, 2021

(30) Foreign Application Priority Data

Jun. 17, 2019    (TW) .................................. 108120865

(51) Int. Cl.
*A01K 1/01*    (2006.01)
*A61B 5/00*    (2006.01)
*G06T 7/00*    (2017.01)

(52) U.S. Cl.
CPC .......... *A01K 1/0107* (2013.01); *A61B 5/0077* (2013.01); *A61B 5/48* (2013.01); *A61B 5/746* (2013.01); *G06T 7/0012* (2013.01); *A61B 2503/40* (2013.01); *A61B 2560/02* (2013.01); *A61B 2560/06* (2013.01); *A61B 2562/02* (2013.01); *G06T 2207/30004* (2013.01)

(58) Field of Classification Search
CPC .............. A01K 1/0107; A61B 2503/40; G06T 2207/10024
USPC ......................................................... 119/165
See application file for complete search history.

(56) References Cited

U.S. PATENT DOCUMENTS

| | | | |
|---|---|---|---|
| 2016/0223552 A1* | 8/2016 | Kizuka | G01N 33/57419 |
| 2018/0368818 A1* | 12/2018 | Oguri | E03D 11/13 |
| 2020/0042780 A1* | 2/2020 | Hori | G06F 18/2178 |
| 2021/0062491 A1* | 3/2021 | Cao | E03D 9/08 |
| 2021/0219871 A1* | 7/2021 | Hochman | A61B 5/742 |

FOREIGN PATENT DOCUMENTS

| | | |
|---|---|---|
| CN | 104008367 | 5/2018 |
| TW | M564907 | 8/2018 |

* cited by examiner

*Primary Examiner* — Fabricio R Murillo Garcia
(74) *Attorney, Agent, or Firm* — Che Yang Chen

(57) ABSTRACT

An intelligent defecation device for living creature includes a device body, a supporting portion, an image module, and a first analysis module. The supporting portion is formed within the inner side of the device body for accommodating a moisture absorption member so as to allow the living creature to leave over its excrement therein. The image module is also arranged at the device body for dynamically capturing the images of the excrement in the supporting portion and outputting the image. The first analysis module is arranged in the device body and connected with the image module to analyze and calculate the defecation mode with the image based on preset or accumulated data, so as to generate a signal when an abnormal defecation mode is diagnosed.

2 Claims, 3 Drawing Sheets

INTELLIGENT DEFECATION DEVICE FOR LIVING CREATURE

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The intelligent defecation device for living creature of the present invention is an artificial Intelligence device that is capable of analyzing defecation mode through dynamically capturing the images of the excrement.

Description of Related Arts

Pets or economic animals play a more and more important role in human life nowadays. In order to properly take care of the animals, the owners always generously do their best to maintain a nice and clean living environment for them and expect to timely understand and manage their health conditions accordingly.

For example, Taiwan Pat. No. M564907 provides a smart living creature defecation device which is capable of dynamically analyzing and calculating the defecation mode with the load weight and the defecation time of the living creature, so as to allow the owners to timely and promptly understand and manage the health conditions of their pets or economic animals accordingly by using the device without causing any adverse effect to the cleanliness of the living environment thereof.

In order to deal with the fierce competition in the market, product providers are always eager to invest in research and development so as to create more functional products that better meet the pet owners' demand.

SUMMARY OF THE PRESENT INVENTION

In order to achieve the above and the other objects, the present invention provides an intelligent defecation device for living creature for living creature that can conduct calculations and analyses of defecation modes through captured images.

The intelligent defecation device for living creature of the present invention includes a device body, a supporting portion, an image module, and a first analysis module. The supporting portion is formed in an inner side of the device body for accommodating a moisture absorption member, so as to allow the living creature to leave over the excrement on the moisture absorption member. The image module is also arranged on the device body for dynamically capturing the images of the excrement in the supporting portion so as for outputting a corresponding image information. The first analysis module is arranged in the device body and connected with the image module to analyze and calculate a defecation mode with the image information based on preset or accumulated data, so as to generate a signal when an abnormal defecation mode is diagnosed.

According to one embodiment, the first analysis module comprises a convolution unit, a pooling unit and a fully connected unit, wherein the convolution unit sequentially matriculates a portion of the image information in order to extract the characteristics, edges, shapes, and/or colors of the excrement, wherein the pooling unit selects maximum values of a calculation result of the convolution unit so as to counter noise, wherein the fully connected unit flattens the calculation result of the pooling unit.

In contrast to prior art, the intelligent defecation device for living creature of the present invention is capable of dynamically capturing the image of the excrement left on the moisture absorption member, so as to conduct calculations and analyses of defecation modes by means of image analytic technology, which allows the device to output more accurate, real, and authentic results to the owner or other external entity and helps the owner to understand the health condition of the pet or economic animal by using the device more precisely.

Please refer to the following detail illustration and figures of the present invention for further understanding of the features and technologies of the present invention. Nevertheless, these appended drawings are just for being references, rather than limits to the present invention.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following disclosure is to illustrate implementations of the intelligent defecation device for living creature according to the present invention through specific embodiments, so that those skilled in the art can understand the advantages and functions of the present invention through the disclosure. The present invention may also be implemented or applied through other different embodiments and the details disclosed in the present specification may be modified and change without deviating from the concept of the present invention for various perspectives and applications. In addition, it is worth mentioning that the drawings of the present invention are only to provide simple schematic illustration, rather than to depict based on actual dimensions. The following embodiments will further illustrate relative technical details of the present invention, but the disclosure shall not limit the scope of the present invention.

Person skilled in the art should be able to understand that though terms, such as "first", "second", "third", and etc., are utilized in the present specification for describing various elements or signals, these elements or signals shall not be limited by these terms. These terms are mainly for distinguishing an element for another element or a signal from another signal. In addition, the term "or" utilized in the present specification may refer to the combinations of any one or more of the listed/specified items depending on actual situations. The power source and mechanical systems utilized for supporting the mechanisms or modules of the present invention will not be specified because they are not directly related to the technical improvement of the present invention.

Figure 1:
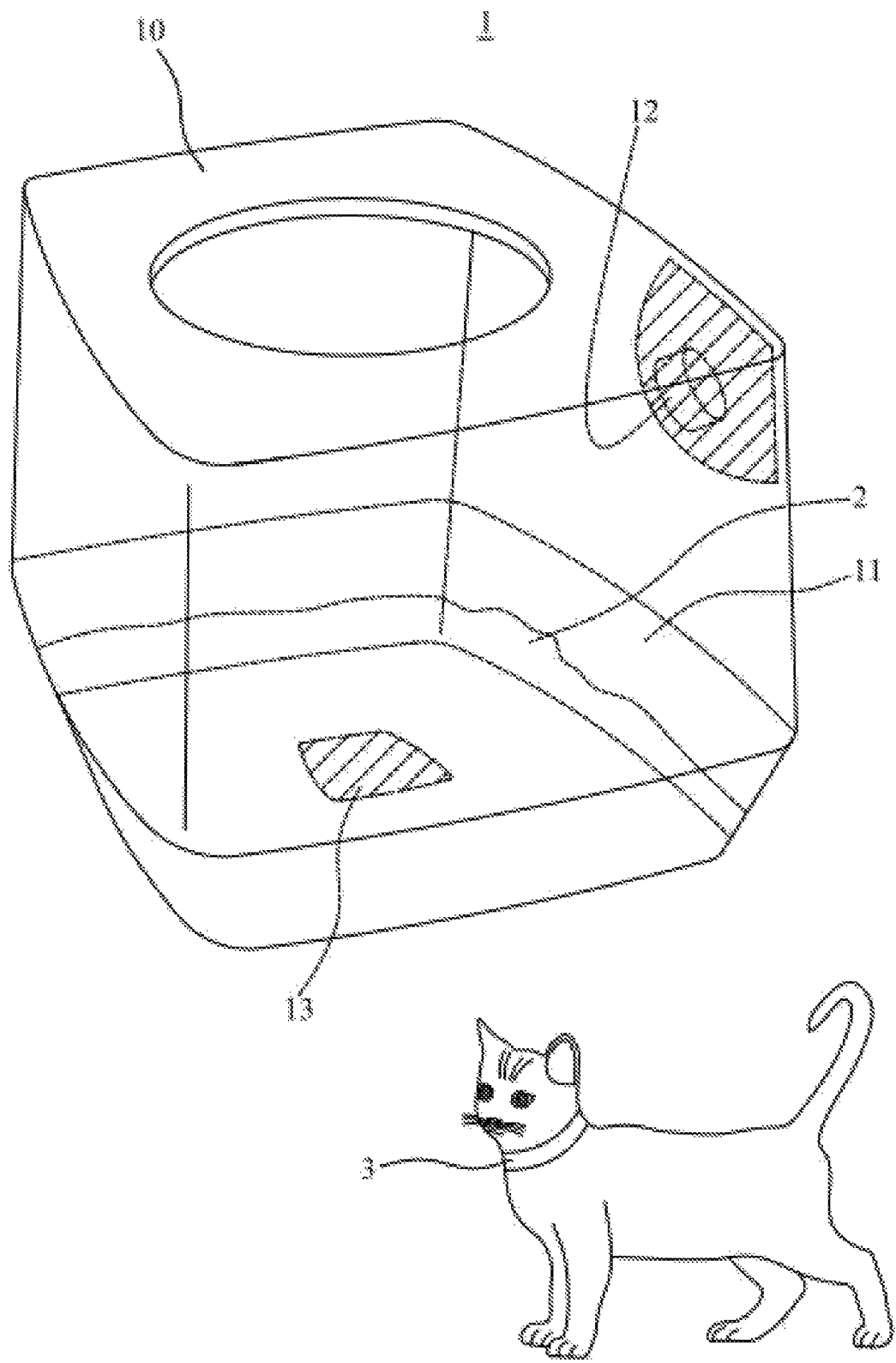
FIG. 1 is a schematic view illustrating an intelligent defecation device for living creature and an application scenario thereof according to a preferred embodiment of the present invention.
Figure 2:
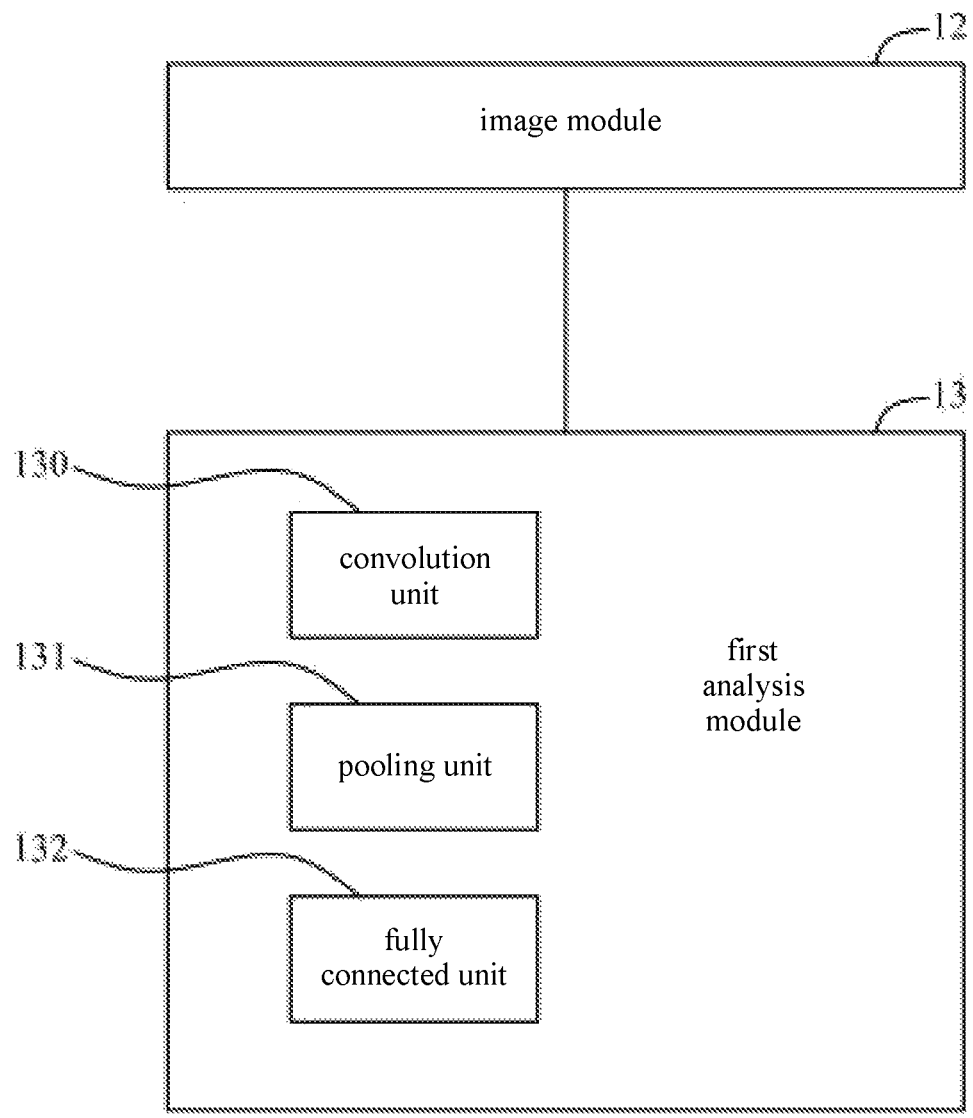
FIG. 2 is a block diagram illustrating the intelligent defecation device for living creature according to the above preferred embodiment of the present invention.
Figure 3:
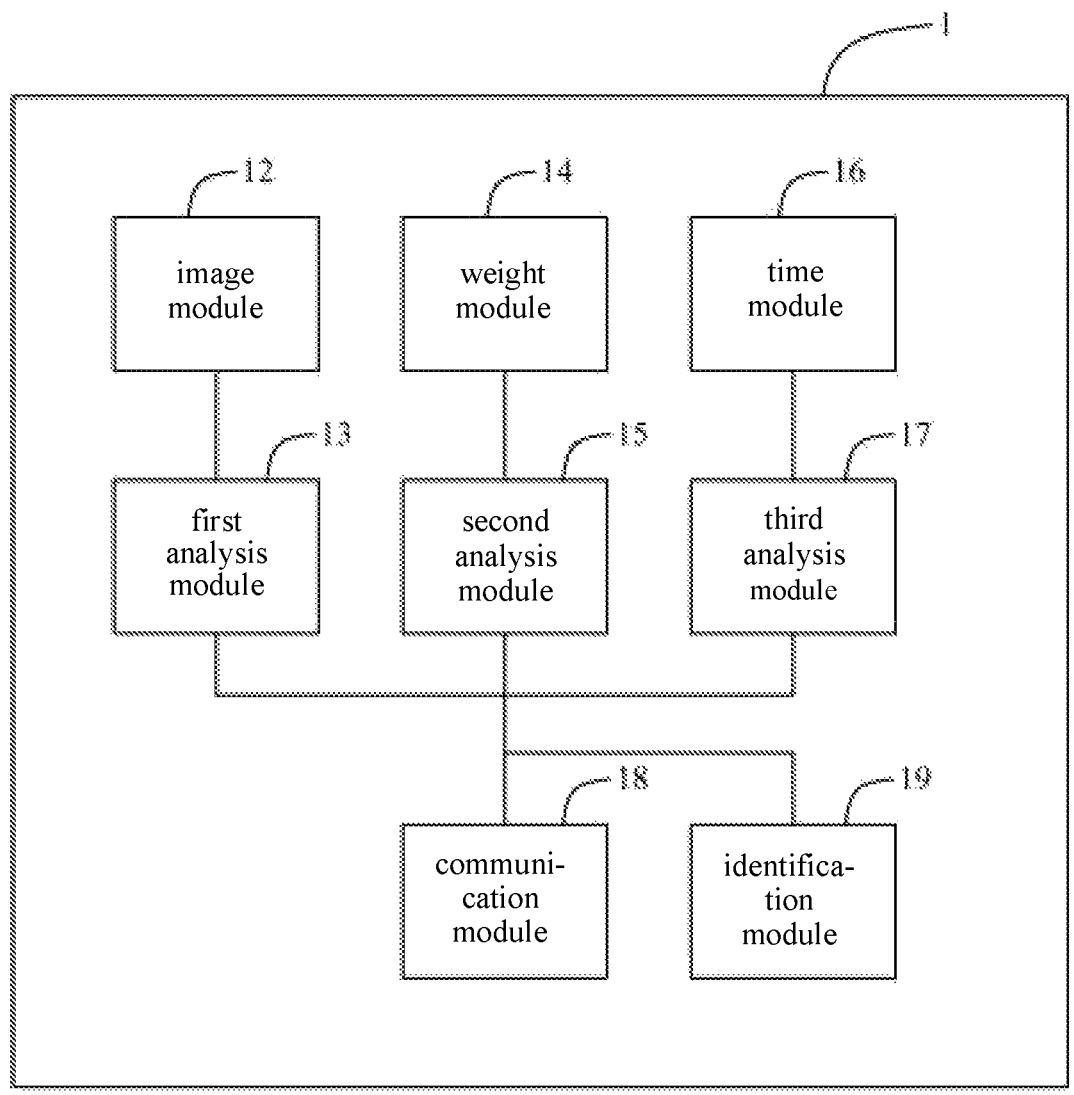
FIG. 3 is another block diagram illustrating the intelligent defecation device for living creature according to the above preferred embodiment of the present invention.

Referring to FIGS. 1-3, FIG. 1 is a schematic view illustrating an intelligent defecation device for living creature and an application scenario thereof according to a preferred embodiment of the present invention. FIG. 2 is a block diagram illustrating the intelligent defecation device for living creature according to the above preferred embodiment of the present invention. FIG. 3 is another block diagram illustrating the intelligent defecation device for living creature according to the above preferred embodiment of the present invention.

Referring to the FIGS. 1-3, the intelligent defecation device 1 for living creature includes a device body 10, a supporting portion 11, an image module 12, and a first analysis module 13. The supporting portion 11 is formed in an inner side of the device body 10 for accommodating a moisture absorption member 2 so as to allow at least a living creature such as a pet or an economic animal to leave over its excrement on the moisture absorption member 2. The image module is 12 is arranged at the device body 10 in such a manner for dynamically capturing the images (not shown) of the excrement in the supporting portion 11 and outputting an image information thereof. The first analysis module 13 is arranged in the device body 10 and connected with the image module 12 in a wired or wireless manner, so as to analyze and calculate the defecation mode with the image information based on preset or accumulated data (stored in an internal or external database), so as to generate a signal when an abnormal defecation mode is diagnosed.

The device body 10 can be in a barrel, tub, or dish shape and is an integral or assembled structure. The supporting portion 11 defines a cavity having a circular shape, oval shape, or polygonal shape, and has an opening on a side or a top of the device body. The image module can be a charge-coupled device (CCD) sensor unit or complementary-metal-oxide semiconductor (CMOS) sensor unit that has an active or passive angle adjustment mechanism or shifting mechanism. The term "living creature" may refer to a household pet, such as cat, or an economic animal, and then the sizes of the device body 10 and the supporting portion 11 can be adjusted accordingly. The moisture absorption member 2, which can be made of non-woven fabric, sand grains, corks, and etc., can be completely laid on a bottom of the supporting portion 11. According to one embodiment, the first analysis module 13 comprises a convolution unit 130, a pooling unit 131 and a fully connected unit 132. The convolution unit 130 sequentially matriculates a portion of the image information (for example starting from a lower right corner and shifting leftwardly and upwardly) captured by the image module 12 in order to extract characteristic(s), edge(s), shape(s), and/or color(s) of the excrement. The pooling unit 131 proceeds a selection of one or more maximum values of a calculation result of the convolution unit 130 to counter noise. The fully connected unit 132 flattens the calculation result of the pooling unit. In practice, the coordination of the supporting portion, the image module, and the analysis module should conduct multi-layer operation of artificial intelligence based on the framework of convolution neural network. For instance, if the excrement in the image is covered by sand gravel, then it has to sequentially capture image blocks of various positions and utilize the multi-layer operation of artificial intelligence to restore the image(s) of the uncovered excrement so as for the comparison to the images of the internal or external databases for the calculation and analysis of the defecation mode.

According to another embodiment, the first analysis module 13 may utilize sliding window mathematical operation method to provide various group recombinations for the convolution unit 130 in order for distinguish the characteristics, such as shapes, edges, corners, and etc., of the excrement. These characteristic are regarded as the basis of the identification and then the pooling unit 131 and the fully connected unit 132 are coordinated to utilize mechanical learning features to redistinguish the shapes and colors of the excrement, so as to further calculate and analyze the health conditions of the pet or economic animal with respect to the left over excrement thereof. For instance, it may recognize if the water content of the excrement higher than a normal range, if there are too many caked masses, if there is blood, and etc., so as to help to identify the health condition of the pet or economic animal.

According to another embodiment, the first analysis module 13 may also utilize artificial intelligence to generate a generative adversarial network and a deconvolution network. In other words, the pooling unit 131 and the fully connected unit 132 may preliminary restore the image captured by the image module 12 into multiple versions according to the weights and the characteristics of the excrement, and then a binary data model is utilized to compare and select a best restored photo, so as to achieve the effect of the elimination of the mantle matter or noise. Next, the weights of the characteristics of mechanical learning can be applied to distinguish the health conditions of the pet or economic animal with respect to the left over excrement thereof.

According to another embodiment, the intelligent defecation device for living creature 1 further comprises a weight module 14 and a second analysis module 15. The weight module 14 is arranged in the device body 10 so as to dynamically detect and record the load weight of the supporting portion 11. The second analysis module 15 is arranged in the device body 10 and connected with the weight module 14 so as to analyze and calculate the defecation mode with the load weight and the defecation time of the living creature based on artificial intelligence and preset or accumulated data (from internal or external database(s)). The first analysis module 13 and the second analysis module 15 can interactively operate to generate a signal when an abnormal defecation mode is diagnosed. The weight module 14 can be uniformly arranged on the bottom of the intelligent defecation device for living creature 1.

According to another embodiment, the intelligent defecation device for living creature 1 further comprises a time module 16 and a third analysis module 17, wherein the time module 16 is arranged in the device body 10 so as to dynamically detect and record the defecation time and duration of the living creature. The third analysis module 17 is arranged in the device body and connected with the time module 16 so as to analyze and calculate the defecation mode with the defecation time and duration based on artificial intelligence and preset or accumulated data (from internal or external database(s)). The first analysis module 13 and third analysis module 17 operate interactively in order to generate a signal when an abnormal defecation mode is diagnosed. The time module 16 records the starting point, end point, interval time, and etc. of the living creature that utilizes the intelligent defecation device 1 for living creature.

The first analysis module 13, the second analysis module 15, and the third analysis module 17 can be selectively utilized and combined in order to achieve an accuracy of the calculation and analysis suitable for the needs of the user the most. Besides, the first analysis module 13, the second analysis module 15 and the third analysis module 17 can utilize artificial intelligence algorithms, such as support vector machine algorithms, random forest algorithms, or recurrent neural network algorithms with internal or external database(s) for the calculations and analyses of defecation modes.

The intelligent defecation device for living creature 1 may also include a communication module 18 arranged for the first analysis module 13, the second analysis module 15, or the third analysis module 17 to communicate with an external smart device (not shown in the figures). The communication module 18 can be a wired or wireless network port or network card. The external smart device may be the pet owner's smartphone or an IOT household smart speaker. The intelligent defecation device for living creature 1 may also include an identification module 19 for reading and identifying information of the external creature accessory 3. The living creature accessory 3 may include a RFID chip, Bluetooth chip or specific magnetic unit, so as to allow the identification module 19 to identify the living creature that approaches and uses the intelligent defecation device 1 through reading the living creature information of the RFID chip or Bluetooth chip or reading the magnetic data from the magnetic unit. Therefore, it avoids mistaken data pairing when there are multiple creatures using the device 1.

In view of above, because the intelligent defecation device 1 for living creature of the present invention is able to rely on the coordination of the supporting portion, the image module, and the analysis module as well as the diverse analytical models and artificial intelligence algorithms, to timely notice the owner or relative third party when the defecation mode of the living creature using the defecation device 1 is diagnosed abnormal (e.g. Gastrointestinal anomalies) by means of the artificial intelligence image analysis, so as to effectively prevent late hospitalization that renders unwanted regrets and mental and physical stresses of the pets, economic animals, and owners. Furthermore, the intelligent defecation device 1 for living creature of the present invention may also include a weight module and a time module, so as to launch a multi-dimensional artificial intelligence calculation with the information of image, weight, and/or time, in order to provide even better accuracy to meet the user's demand.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An intelligent defecation device for living creature, comprising:
    a device body;
    a supporting portion being provided within an inner side of said device body and accommodating a moisture absorption member in such a manner to allow an excrement of the living creature to be left on said moisture absorption member;
    an image module, arranged at said device body for dynamically capturing one or more images of the excrement in said supporting portion and outputting an image information of the excrement;
    a first analysis module arranged in said device body and connected with said image module, to analyze and calculate a defecation mode with the image based on preset or accumulated data, so as to generate a signal when an abnormal defecation mode is diagnosed, wherein said first analysis module comprises a convolution unit, a pooling unit and a fully connected unit, wherein said convolution unit sequentially matriculates a portion of the image information in order to extract one or more characteristics, edges, shapes, and/or colors of the excrement, wherein said pooling unit selects one or more maximum values of a calculation result of said convolution unit so as to counter noise, wherein said fully connected unit flattens the calculation result of said pooling unit; and
    a weight module and a second analysis module, wherein said weight module is arranged in said device body for dynamically detecting and recording a load weight of said supporting portion, wherein said second analysis module is arranged in said device body and connected with said weight module so as to analyze and calculate the defecation mode with the load weight and a defecation time based on preset or accumulated data, wherein said first analysis module and said second analysis module operate interactively in order to generate the signal when the abnormal defecation mode is diagnosed.

2. The intelligent defecation device, as recited in claim 1, further comprising an identification module arranged for identifying and reading an external smart accessory.

* * * * *